US012745944B2

(12) United States Patent
Franck

(10) Patent No.: US 12,745,944 B2
(45) Date of Patent: Sep. 29, 2026

(54) PHYSIOLOGICAL MEASUREMENT DEVICE, SYSTEM AND METHOD

(71) Applicant: KONINKLIJKE PHILIPS N.V., Eindhoven (NL)

(72) Inventor: Christoph Florian Franck, Magstadt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 274 days.

(21) Appl. No.: 18/717,512

(22) PCT Filed: Nov. 29, 2022

(86) PCT No.: PCT/EP2022/083556
§ 371 (c)(1),
(2) Date: Jun. 7, 2024

(87) PCT Pub. No.: WO2023/104576
PCT Pub. Date: Jun. 15, 2023

(65) Prior Publication Data

US 2025/0049371 A1 Feb. 13, 2025

(30) Foreign Application Priority Data

Dec. 9, 2021 (EP) .................................... 21213378

(51) Int. Cl.
*A61B 5/308* (2021.01)
*A61B 5/00* (2006.01)
(Continued)

(52) U.S. Cl.
CPC .............. *A61B 5/308* (2021.01); *A61B 5/305* (2021.01); *A61B 5/31* (2021.01); *A61B 5/7217* (2013.01); *A61B 5/725* (2013.01)

(58) Field of Classification Search
None
See application file for complete search history.

(56) References Cited

U.S. PATENT DOCUMENTS 6,810,283 B2 10/2004 Suribhotla
11,147,517 B2 * 10/2021 Franck ................ A61B 5/7203
2018/0092563 A1 4/2018 Matthiesen

FOREIGN PATENT DOCUMENTS

WO 2018162365 A1 9/2018
WO 2020073781 A1 4/2022

OTHER PUBLICATIONS

Samiei et al., "A Bidirectional Neural Interface SoC With Adaptive IIR Stimulation Artifact Cancelers," Jul. 2021, IEEE Journal of Solid-State Circuits, vol. 56, No. 7, 2142-2157. (Year: 2021).*

(Continued)

*Primary Examiner* — Michael W Kahelin

(57) ABSTRACT

The present invention relates to a physiological measurement device, system and method. The device (11) comprises multiple input channels (15) configured to obtain multiple measurement signals ($s_i$) acquired from a subject; a recording unit (10) configured to filter the multiple measurement signals ($s_i$) by use of a digital filter and calculate multiple vector signals ($y_j$) from the multiple filtered measurement signals; a stimulation unit (20) configured to generate one or more stimulation signals ($w_k$) for electrically stimulating tissue of the subject; multiple output channels (22, 32) configured to output the multiple vector signals ($y_i$) and the one or more stimulation signals ($w_k$); and a processing unit (27) configured to determine adjusted filter coefficients of the digital filter during or after the generation and output of the one or more stimulation signals ($w_k$) based on the current filter coefficients, the one or more stimulation signals ($w_k$) and the multiple measurement signal ($s_i$) acquired while the one or more stimulation processing stimulation signals ($w_k$) are outputted for stimulation.

18 Claims, 6 Drawing Sheets

(51) Int. Cl.
*A61B 5/305* (2021.01)
*A61B 5/31* (2021.01)

(56) References Cited

OTHER PUBLICATIONS

International Search Report Dated Feb. 20, 2023 For International Appln No. PCT/EP2022/083556 Filed Nov. 29, 2022.
Samiei Aria et al: "A Bidirectional Neural Interface Soc With Adaptive IIR Stimulation Artifact Cancelers", IEEE Journal of Solid-State Circuits, IEE, USA vol. 56, No. 7, Feb. 9, 2021, pp. 2142-2157.
S. Stanslaski et al: "Design and Validation of a Fully Implantable, Chronic, Closed-Loop Neuromodulation Device With Concurrent Sensing and Stimulation", Jul. 2012, IEEE Transactions on Neural Systems and Rehabilitation Engineering, pp. 410-421.
Malekzadeh-Arasteh, Omid, et al: "An Analysis of CMRR Degradation in Multi-Channel Biosignal Recording Systems", 2021, IEEE Transactions on Circuits and Systems, pp. 151-155.

* cited by examiner

PHYSIOLOGICAL MEASUREMENT DEVICE, SYSTEM AND METHOD

CROSS-REFERENCE TO PRIOR APPLICATIONS

This application is the U.S. National Phase application under 35 U.S.C. § 371 of International Application No. PCT/EP2022/083556, filed on Nov. 29, 2022, which claims the International application Ser. No. 21/213,378.9 filed on Dec. 9, 2021. These applications are hereby incorporated by reference herein.

FIELD OF THE INVENTION

The present invention relates to a physiological measurement device, system and method, in particular for taking and/or processing physiological measurements such as electrophysiological measurements like an electrocardiogram (ECG) or an electroencephalogram (EEG).

BACKGROUND OF THE INVENTION

Physiological measurement devices usually present measurement results to their users, e.g. medical personnel, in the form of differential values—often referred to as "vectors" or, in particular in the context of ECG or EEG, as "leads". The differential values are derived from the difference of physical quantities measured at different points on a patient's body. The measurement devices are designed to suppress a common mode component of signal measured at the different points as good as possible. Common-mode interference is a major cause for artefacts in electrophysiological recordings. Such artefacts degrade the usefulness of the recording for purposes like diagnosis, therapy, and non-medical analysis.

In WO 2018/162365 A1, a physiological measurement device is described that includes digital filters arranged at outputs of different Analog-to-Digital Converters (ADCs) associated with different channels of the measurement device. The filters are calibrated for reduced common mode interference. A respective calibration method comprises determining a reference input channel and minimizing time-domain differences between the reference input channel and each input channel other than the reference input channel.

SAMIEI ARIA ET AL: "A Bidirectional Neural Interface SOC With Adaptive IIR Stimulation Artifact Cancelers", IEEE JOURNAL OF SOLID-STATE CIRCUITS, IEEE, USA, vol. 56, no. 7, 9 Feb. 2021 (2021-02-09), pages 2142-2157, XP 011863307, discloses a 180-nm CMOS bidirectional neural interface system-on-chip that enables simultaneous recording and stimulation with on-chip stimulus artifact cancelers. The front-end (FE) cancellation scheme incorporates a least-mean-squares (LMS) engine that adapts the coefficients of a two-tap infinite-impulse-response filter to replicate the stimulation artifact waveform and subtract it at the FE. Each recording channel houses a pair of adaptive infinite-impulse-response filters, which enables the cancellation of the artifacts generated by the simultaneous operation of the two on-chip stimulators.

SUMMARY OF THE INVENTION

It is an object of the present invention to further reduce common mode interference and/or to improve characteristics of the digital filters without compromising common mode rejection capabilities.

In a first aspect of the present invention a physiological measurement device is presented comprising:

multiple input channels configured to obtain multiple measurement signals acquired from a subject;

a recording unit configured to filter the multiple measurement signals by use of a digital filter and calculate multiple vector signals from the multiple filtered measurement signals, wherein a vector signal represents a differential signal and is calculated by forming a linear combination of at least two filtered measurement signals;

a stimulation unit configured to generate one or more stimulation signals for electrically stimulating tissue of the subject;

multiple output channels configured to output the multiple vector signals and the one or more stimulation signals; and a processing unit configured to determine adjusted filter coefficients of the digital filter during or after the generation and output of the one or more stimulation signals based on the current filter coefficients, the one or more stimulation signals and the multiple measurement signal acquired while the one or more stimulation signals are outputted for stimulation, wherein the digital filter is configured to filter the multiple measurement signals, after the adjusted filter coefficients have been determined, by use of the adjusted filter coefficients.

In a further aspect of the present invention a physiological measurement system is presented comprising:

multiple measurement electrodes configured to acquire multiple measurement signals from a subject;

a physiological measurement device as defined in any one of the preceding claims;

multiple stimulation electrodes configured to apply one or more stimulation signals generated by the physiological measurement device to the subject for electrically stimulating tissue of the subject; and an output configured to output multiple vector signals calculated by the physiological measurement device.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed system, in particular as defined in the dependent claims and as disclosed herein.

One of the ideas of the present invention relates to the use of a stimulator component (also called stimulation unit) that generates one or more stimulation signals for electrically stimulating tissue of the subject in a physiological measurement device. It has been found that the common-mode interference generated by the stimulation unit offers the opportunity to modify the input channel transfer function of the recorder component (also called recording unit) in order to achieve better common-mode signal cancellation, both for interference generated by the device itself as well as for interference from external sources.

Common-mode interference may be a particular problem in stimulator/recorder devices, as the action of the stimulator component itself can create large common-mode signals at the inputs of the recorder component. This aspect becomes more critical if the device needs to observe the immediate reaction to the stimulation. This problem can be overcome by the present invention by using the interference caused by the stimulator action to update digital filter coefficients for improved common-mode rejection of the recorder component. The physiological measurement device, system and method according to the present invention thus exploit the fact that it is known when stimulation activity occurs and, hence, when the input channels are picking up the (usually large) stimulation signal.

In an embodiment the processing unit is configured to compute the adjusted filter coefficients on a sample-by-sample basis (e.g. using a least-mean-squares or recursive-least-squares algorithm) or block-wise (e.g. using an optimization algorithm). Block-wise algorithms are easier to use and have an established mathematical framework behind them. They can easily work with a variety of constraints and different cost functions. Their disadvantage is that the algorithm needs to keep all the data that is being worked on in memory, and that the update of the filter coefficients can result in abrupt changes in filter behavior. The latter can be somewhat remedied by a constraint that limits the difference between the current and the new filter coefficients. Online/sample-by-sample algorithms tend to have a smaller memory/RAM footprint, as less data is kept in memory. Their mathematical properties like convergence and stability are more difficult to establish, especially for more complex cost functions. It is also more difficult to integrate constraints into a sample-by-sample algorithm. A sample-by-sample algorithm tends to be a more elegant and economical solution, but unless the cost function and constraints are very simple, or better mathematical theory emerges, applications are more likely to use block-wise algorithms.

In another embodiment the processing unit is configured to compute the adjusted filter coefficients by minimizing a cost function to reflect the magnitude of common-mode interference. A simple measure like the energy contained in the vector signals may be used as the magnitude.

In a practical implementation the recording unit comprises an analog filter for analog filtering of the multiple (preferably analog) measurement signals, an analog-to-digital converter for converting the filtered measurement signals into digital signals, in particular in single-ended mode, and a digital filter for digital filtering of the digital signal to generate the multiple vector signals.

The processing unit may be configured to determine adjusted filter coefficients after each stimulation event or after a predetermined or arbitrary number of stimulation events. Thus, in can be predetermined or individually controlled how often the filter coefficients shall be updated.

The physiological measurement device may further comprise a memory device configured to store multiple different sets of filter coefficients related to one input channel, wherein the processing unit is configured to select one of the different sets of filter coefficients for determining the adjusted filter coefficients. In an implementation, multiple vector signals may be defined and the memory device may be configured to store the different sets of filter coefficients for one input channel, wherein at least some, preferably each, of the stored sets of filter coefficients are associated with a different one of the multiple vector signals.

In another embodiment the processing unit is configured to calculate multiple vector signals, one of said multiple vector signals being calculated from multiple filtered measurement signals based on a definition vector, wherein the memory device is configured to store different sets of filter coefficients related to one input channel, and wherein the processing unit is configured to select one of the different sets of filter coefficients for calculating a specific vector signal.

In yet another embodiment the processing unit is configured to generate samples of one or more stimulation signals applied to the multiple input channels, input at least one definition vector describing a linear combination of samples of at least two input channels, optimize a metric calculated from at least one vector signal, the vector signal being based on the samples of the one or more stimulation signals and the definition vector, and obtain, based on the optimizing, at least one set of filter coefficients for at least one digital filter associated with a specific input channel. Hereby, the processing unit may preferably be configured to input multiple definition vectors and to obtain at least one set of filter coefficients for a specific input vector. By optimizing the metric not only based on the samples of the measurement signal but also on the definition vectors, the selection of a reference signal can be omitted, thereby yielding well-suited sets of filter coefficients for the individual digital input filters that allows for good common-mode interference mitigation and has particularly low adverse effect with the quality of desired, e.g. differential, component of a vector signal.

The processing unit may further be configured to optimize the metric by multiple optimizing steps, wherein a set of filter coefficient obtained by one optimizing step being kept as constant for a subsequent optimizing step and/or by use of at least one linear equality constraint with respect to a filter coefficient and/or by use of at least one nonlinear inequality constraint for limiting a gain of a certain digital filter at a given frequency. Thanks to basing the optimization on both the samples of the measurement signals as well on the definition vectors, constraints may be defined to control characteristics of at least one input filter which may not or not directly related with common-mode interference reduction. For example, the optimizing may subject to at least one linear equality constraint with respect to a filter coefficient. Such linear equality constraints may be applied to obtain a certain DC gain or a certain gain at the Nyquist frequency.

The method may comprise inputting a DC gain value of at least one input channel and determining a corresponding linear equality constraint based on the DC gain value. When setting the DC gain of one, multiple, or all, digital input filters based on the inputted DC gain values, differences between the channels can be compensated. In an embodiment, the DC gain value of one input channel is input and a corresponding linear equality constraint may be determined based on that single DC gain value. The DC gain value may be determined by a separate measurement process performed prior to the present method or in parallel to the present method. Applying at least one linear equality constraint, e.g. based on the DC gain value, prevents the optimizing operation form arriving at a trivial solution that minimizes the target function by simply setting all filter coefficients to zero.

Moreover, the optimizing may be subject to at least one nonlinear inequality constraint for limiting a gain of a certain input filter at a given frequency. Such constraint(s) allow to control the frequency response of the digital input filter at least to some extent. These constraints may be defined such that an undesired frequency response, e.g. of parts of an analog frontend, can be at least partly compensated.

The optimizing may also be subject to at least one bounds constraint with respect to filter coefficients. Such constraints limiting the range of the filter coefficients may avoid numerical overflows when storing the filter coefficients according to a specific digital format (e.g. a certain floating point format or a certain fixed point format). Such constraints further may limit the gain of a specific input filter at a certain frequency, e.g. to avoid amplification of unimportant frequency ranges.

In another embodiment the processing unit may be configured to sample the one or more stimulation signals at a sampling rate that is increased compared to an operating sampling rate applied to perform physiological measurements by the physiological measurement device and/or with a resolution that differs from a measurement resolution of samples received to perform the physiological measurements. The so adapted sampling rate and/or resolution is well-suited for calibration because higher frequencies can be considered more accurately, whereas a lower resolution may be acceptable during calibration because the amplitude of the test signal can be better controlled than the amplitude of measured signals captured during normal operation of the measurement device.

The processing unit may further be configured to optimize the metric by minimizing a penalty function of output samples, the output samples corresponding to at least one vector signal calculated from the stimulation signal filtered according to the filter coefficients and from the definition vector, in particular by minimizing multiple different penalty functions of the output samples simultaneously or minimizing a scalar target function of different penalty functions.

The vector signal corresponding to a differential measurement is often also referred to as "vector". Moreover, a stimulation signal applied may be the same at all input channels. Accordingly, a pure common-mode signal is applied to the channels of the measurement device. Minimizing the norm of at least one vector signal then corresponds to maximizing common-mode reduction. The output samples may correspond to a single, multiple or all vector signals supported by the measurement device. When using dedicated sets of filter coefficients for the individual vector signals or for predefined groups of multiple vector signals, the output samples may correspond to the respective vectors signal or to the respective group of vectors signals.

Optimizing may comprise to minimizing multiple penalty functions of the output samples simultaneously or minimizing a scalar target function of different penalty functions. In other words, the optimization may be a multi-object optimization.

At least one penalty function may be a convex or quasi-convex penalty function, preferably a norm. For example, the 1-infinity (maximum) norm and another norm, preferably the 12 (Euclidean) norm may be minimized simultaneously or based on the scalar target function. At least one penalty function may comprise the Huber loss function.

It also possible that optimizing comprise minimizing a scalar target function of different norms or other penalty functions to reduce the computational complexity of the optimization. Composing a target function from several different norms or penalty functions may allow to achieve multiple objectives or trade off different objectives against each other. For example using a weighted sum of the 1-infinity norm and the 1-2 norm would minimize the maximum deviation (quantified by the 1-infinity norm) but also the energy content of an error signal (quantified by the 12 norm) with the balance of the tradeoff given by the weight.

In another embodiment the processing unit is configured to use the multiple measurement signals to modify and/or monitor the effect of the stimulation, in particular to determine one or more stimulation parameters including one or more of amplitude, timing and shape of the one or more stimulation signals. This enables closed-loop neuromodulation applications.

The publication of Samiei et al. cited above describes the use of an adaptive digital filter to "learn" the shape of the artefact produced by stimulation pulses, and in a second step use the trained filter as a predictor to generate an estimate of the current value of an applied stimulation pulse, use this prediction to output a signal via a digital-to-analog converter and subtract this synthetic signal from the input signal in the analog domain. This reduces the magnitude of the stimulation artefact in the analog domain and before analog-to-digital conversion takes place. This may lead to a reduced required dynamic range (input range) of the analog frontend (AFE).

The method disclosed by Samiei et al. acts in response to a stimulation signal, i.e., the system knows when stimulation pulses are about to be applied and can start the signal synthesis and subtraction. The method hence provides no benefit during periods where not stimulation pulses are applied. Also, the adaptive digital filter used in this method is only used for generating the synthetic pulse artefact estimate. It is not applied to the output value, i.e., the signal that is presented to the user or used as input for physiological processing algorithms.

While the present invention uses single-ended amplification and sampling and is not usable with differential amplification and sampling, the method disclosed by Samiei et al. uses differential amplification and sampling, with single-ended amplification and sampling being shown for simplicity.

The method disclosed by Samiei et al. aims to cancel out specific types of artefacts where it is known when they occur, as they are generated by the system itself in the form of stimulation pulses. The present invention, in contrast, reduces the effect of stimulation pulse artefacts, as far as the artefacts have a common-mode signal component. The adjusted filter coefficients are thus applied continuously, not only in response to applied stimulation pulses; only the update of the filter coefficient happens in response to stimulation pulses. The improved symmetry of the input channels helps to cancel out all forms of common-mode interference, including those where the system does not know when they occur.

The method disclosed by Samiei et al. works by actively injecting an estimated inverse of the artefact into the analog signal path in order to cancel out the stimulation artefact. Injecting signals into the input path, may, however, provide the problems that it is easily detectable as such, but leakage currents can flow towards the patient, etc. The present invention aims to avoid such problems and does not inject any compensatory signals into the analog signal path, but the reduction of the interfering signal components may happen by increasing the symmetry of the overall (analog+digital) input channel behavior.

The method disclosed by Samiei et al. aims to reduce the required dynamic range of the analog frontend (amplifiers and analog-to-digital converters). Further, it aims to reduce both common-mode and differential-mode components of the stimulation pulse artefacts. The present invention, instead, may have a large dynamic range of the input path, which makes it more effective. Further, it only cancels out common-mode interference, but it is not limited to artefacts that are known to occur, like stimulation pulses. It will improve common-mode rejection even during periods where no stimulation pulses are applied.

According to the publication by Samiei et al., the digital filter is used as a predictor to generate an estimate of the stimulation pulse artefact. The adaptive digital filter is, different from the present invention, not applied to the measurement output, but only to the signal that is output via the digital-to-analog converter and injected into the analog signal path. Further, the method disclosed by Samiei et al. takes an active approach to suppress one specific shape of artefact and does not improve common-mode rejection by improving the symmetry of the single-ended input channels.

Finally, according to Samiei et al. the preferred way of forming differential signals is in the analog part of the circuit by using differential amplifiers. Recovering differential signals by calculating a linear combination of single-ended signals, e.g. the difference between single-ended signals. The present invention, in contrast, makes use of single-ended amplification and sampling, so that the adapted digital filters using the adjusted filter coefficients can be applied to each single-ended signal before linear combinations (e.g. differences) of the single-ended signals are calculated digitally.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Closed-loop neuromodulation is an emerging technology that has been proposed for the therapy and management of neurological conditions like Parkinson's disease, epilepsy and spinal cord injuries. The technology is based on devices (also called "stimulator/recorder") that can provide stimulation signals to nerve tissue, and simultaneously record the electrical activity of the tissue in order to initiate, modify and monitor the therapeutic stimulation and its effects. Another application that requires both electrophysiological recording capability and stimulation capability is bi-directional brain-machine-interfaces. Measured electrophysiological signals are used to convey information from the brain to the machine, and targeted electrical stimulation is used to transmit information from the machine to the brain.

Electrophysiological recorders record small electric potential differences occurring between locations on or inside a patient's body due to physiological activity of electrically excitable cells like nerve cells and muscle cells. The potential differences are small (microvolt to millivolt range) and usually superimposed on a comparatively large common-mode signal component (millivolts to volts). The common-mode signal occurs due to external sources, most commonly in the form of power line interference, and it needs to be suppressed in order to avoid artefacts in the physiological recording. The differential mode measurement would in theory provide good suppression of the common-mode signal components. However, due to input channel mismatch, common-mode to differential-mode conversion occurs in real devices. For this reason, real devices employ additional measures to suppress common-mode interference, such as driven reference electrode feedback loops ("right leg drive" in electrocardiography).

The present invention presents a device, system and method for electrophysiological stimulation and measurement of (electro)physiological measurement signal. The invention uses the common-mode artefact generated by the stimulation as a calibration signal to update digital filter coefficients of the recorder component. The adjustment improves the common-mode rejection of the recorder component. This improves the rejection of both the artefact generated by the stimulation as well as of interference from external sources.

Figure 1:
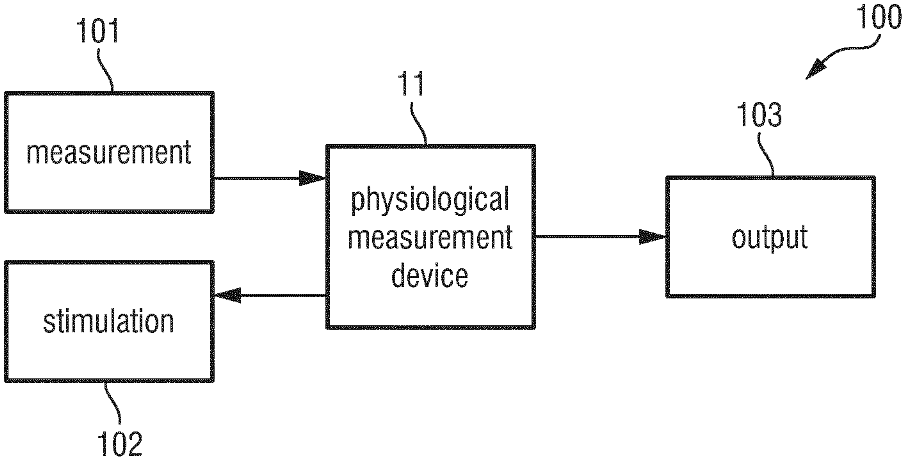
FIG. 1 shows a schematic diagram of an embodiment of a physiological measurement system according to the present invention.

FIG. 1 shows a schematic diagram of an embodiment of a physiological measurement system 100 according to the present invention. It comprises multiple measurement electrodes 101 configured to acquire multiple measurement signals (herein also called input signals; preferably analog input signals) from a subject. It comprises further a physiological measurement device 11, which may e.g. be implemented as or in a processor or computer, in software and/or hardware. Details of the physiological measurement device 11 will be described below. Further, multiple stimulation electrodes 102 are provided that are configured to apply one or more stimulation signals generated by the physiological measurement device 11 to the subject for electrically stimulating tissue of the subject. An output 103 is provided to output multiple vector signals calculated by the physiological measurement device 11. The output 103 may generally be any means that outputs the determined multiple vector signals calculated by the physiological measurement device, preferably in visual form. For instance, the output 103 may be a display, a touchscreen, a computer monitor, the screen of a smartphone or tablet, a printer, etc.

The physiological measurement device 11 may be an electrophysiological measurement device such as an ECG or an EEG. Various configurations, in particular regarding the number N of channels and the number M of output signals are possible.

A comparatively simple example is an ECG or EEG device having a single output signal (single vector) and two electrodes connected to two inputs (two channels). The only definition vector needed for such a measurement device 11 may be $v_1=[1,-1]$.

Figure 2:
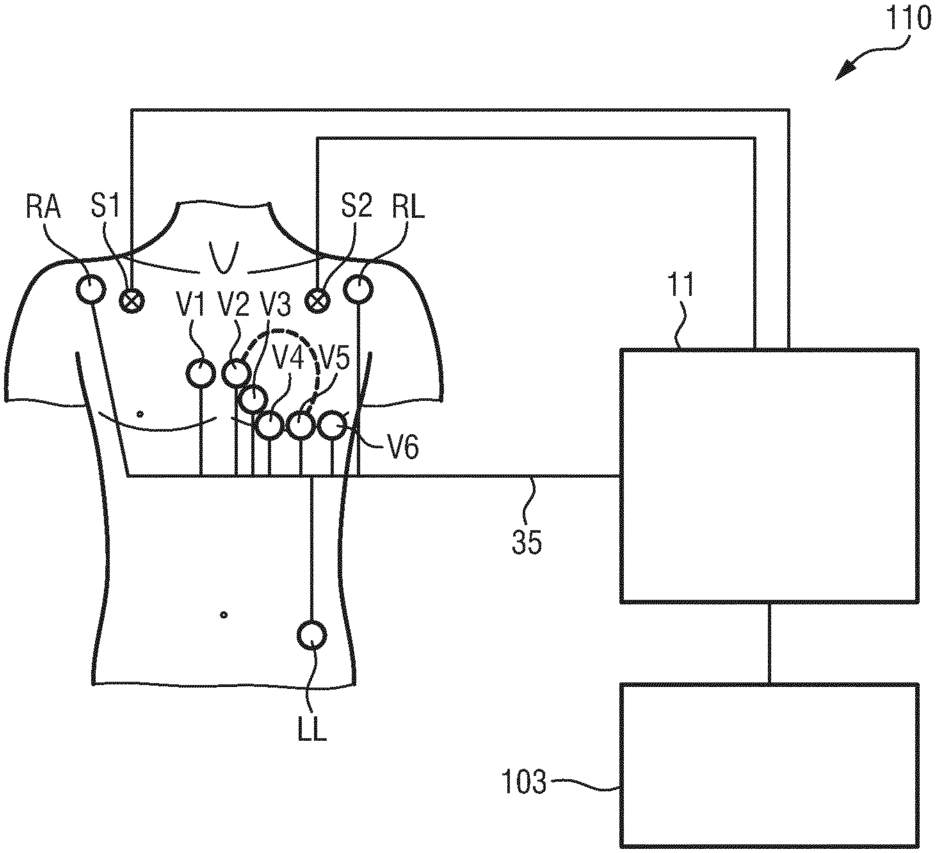
FIG. 2 shows a schematic diagram of an exemplary implementation of a physiological measurement system according to the present invention.

According to another example of a physiological measurement system 110 shown in FIG. 2, a 12-lead ECG is provided having nine measurement electrodes connected to N=9 inputs of the measurement device 11. Such measurement device thus has nine channels. The electrodes may include three limb electrodes (right arm RA, left arm LA, left leg LL), six chest electrodes (V1-V6), which are connected via a measurement cable 35 to nine different inputs of the physiological measurement device 11.

The output vector signals $y_1, \ldots, y_{12}$ may be defined according to twelve leads visualized by means of the output device 103 to medical personnel. The leads and respective vector signals include lead I (LA−RA), lead II (LL−RA), lead III (LL−LA), aVR (RA−0.5*(LA+LL)), aVL (LA−0.5*(RA+LL)), aVF (LL−(RA+LA)), and (Vn−WCT); n=1, . . . , 6. WCT corresponds to the Wilson's central terminal voltage which is approximated as (RA+LA+LL)/3.

Two exemplary stimulation electrodes S1, S2 are provided, in this example attached to the subject's body, in other embodiments implanted into the subject's body. Separate electrodes for recording of measurement signals and injecting the stimulation signal(s) are preferably used, which simplifies the circuitry and excludes the presence of dual-purpose electrodes that require special consideration when updating the filter coefficients.

Stimulation electrodes are e.g. used in neuromodulation, which allows the possibility to treat different pathologies. The term "neuromodulation" is essentially electrical stimulation of the nervous system in order to modulate or modify a specific function (as in movement disorders, pain, epilepsy), and can be delivered in different ways: through stimulation over skin surface, peripheral nerve stimulation, cortical stimulation, or deep brain stimulation. A pulse generator (as part of the physiological measurement device 11 or as external part) is generally used to generate and modify different stimulation settings.

The present disclosure is not limited to the depicted and explained physiological measurement devices. For example a 15-lead or an 18-lead ECG can be provided based on the present disclosure as well. It is also possible to provide a high-density EEG based on the present disclosure having 32 or more channels. Further, different types, numbers and arrangements of stimulation electrodes, depending on the desired application, can be used.

Figure 3:
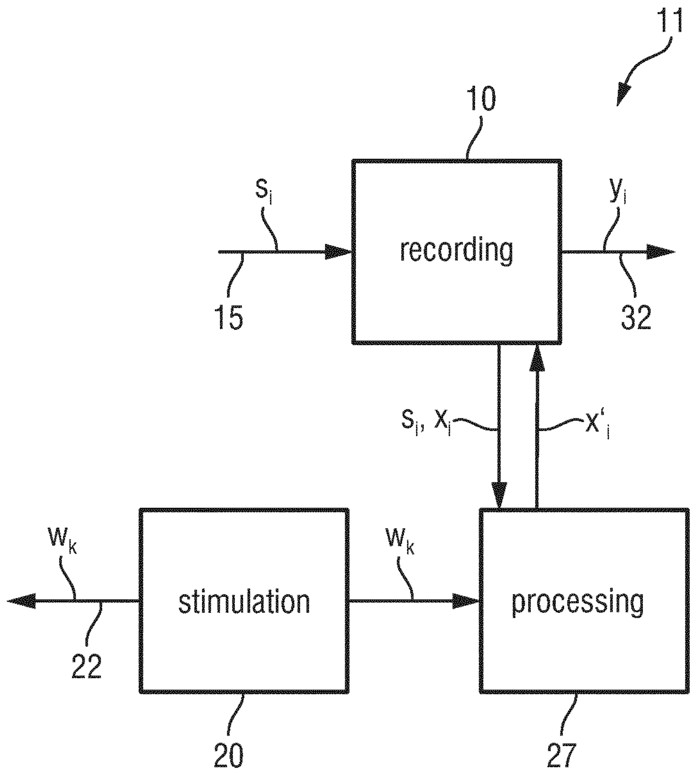
FIG. 3 shows a schematic diagram of an embodiment of a physiological measurement device according to the present invention.

FIG. 3 shows a schematic diagram of an embodiment of a physiological measurement device 11 according to the present invention. It comprises multiple input channels 15 configured to obtain multiple measurement signals $s_i$ acquired from a subject. Preferably, the input channels 15 are directly connected (preferably wired, e.g. via one or more measurement cables) with the measurement electrodes 101.

A recording unit 10 filters the multiple measurement signals $s_i$ by use of a digital filter and calculates multiple vector signals y (also called difference signals) from the multiple filtered measurement signals. The recording unit 10 is preferably configured to pick up electrophysiological signals from a human or animal and to sample the signals in single-ended mode against a common, stable reference This allows individual input channel-specific digital filters to be applied to the recorded signals before differences/vectors/leads are calculated.

A stimulation unit 20 generates one or more stimulation signals $w_k$ for electrically stimulating tissue of the subject. The stimulation unit is preferably configured to deliver stimulation signals to electrically excitable tissue (nerve or muscle tissue) of a human or animal.

Multiple output channels 22, 32 are provided to output the multiple vector signals $y_i$ (to the output 103, e.g. a display) and the one or more stimulation signals $w_k$ (to the stimulation electrodes 102; preferably wired, e.g. via one or more signal cables).

A processing unit 27 determines adjusted filter coefficients $x'_i$ of the digital filter during or after the generation and output of the one or more stimulation signals $w_1$ based on the current filter coefficients $x_i$, the one or more stimulation signals $w_k$ and the multiple measurement signal $s_i$ acquired while the one or more stimulation signals $w_k$ are outputted for stimulation. The processing unit 27 may be implemented by a computer or processor, in hard- and/or software, e.g. as one or more programmed microprocessor(s). The processing unit 27 is further preferably configured to control the recording unit 10 and the stimulation unit 20 and their functionalities.

The processing unit may thus update the coefficients of individual channel-specific digital filters during or after the stimulation unit produces a stimulation signal. This minimizes the appearance of the common-mode stimulation artefact in the difference (vector) signals. Different algorithms may be used for updating the filter coefficients, for example online sample-by-sample optimization (least-mean-squares (LMS) or recursive-least-squares (RLS)), or block-wise optimization.

The present invention is based on the insight that devices with integrated stimulation functionality may generate substantial common-mode signals when generating stimulation signals. Devices with the purpose of providing stimulation signals are subject to less restrictive limits, meaning that the stimulation signals can be large enough to be used for input channel calibration/mismatch compensation. The present invention thus leverages signals generated for the primary purpose of stimulating tissue for the secondary purpose of updating the channel-specific digital filter coefficients.

Figure 4:
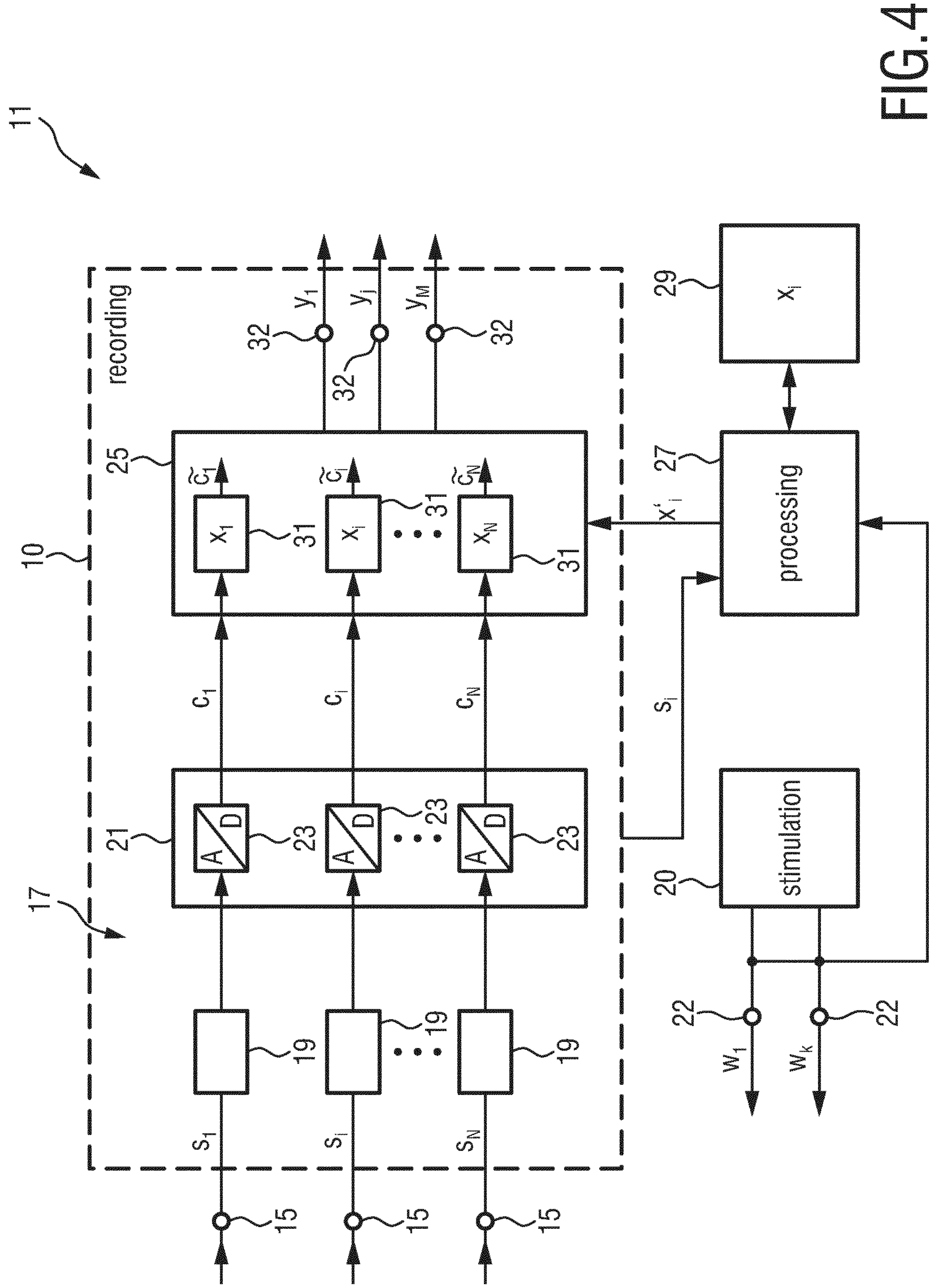
FIG. 4 shows a schematic diagram of another embodiment of a physiological measurement device according to the present invention.

FIG. 4 shows a schematic diagram of another, more detailed embodiment of a physiological measurement device 11 according to the present invention. The recording unit 10 of the physiological measurement device 11 has multiple channels. For the sake of simplicity, only three channels are shown in FIG. 4 but in general N channels may be present. Each channel has an analog input 15 for inputting an analog input signal (the measurement signal) $s_i$(i=1, . . . , N). The inputs 15 of the individual channels are connected to an analog front end 17. The analog front end 17 includes analog input circuitry 19 associated with the individual channels. The analog input circuitry 19 may comprise one or more amplifiers, an impedance converter, an analog filter, or the like. The input circuitry of the individual channels is connected to a multichannel analog to digital converter 21. The multichannel analog to digital converter 21 is configured to convert the individual input signals $s_i$ preprocessed by the individual analog input circuitries 19 into samples $c_i$ i=1, . . . , N which represent the input signals $s_i$ of the individual channels.

In the shown embodiment, the multichannel analog to digital converter 21 comprises multiple analog to digital converters (ADC 23) where each of these ADCs is associated with a specific channel. In another embodiment, a single ADC 23 may be associated with multiple channels and the multichannel analog to digital converter 21 may comprise a multiplexer to selectively connect one channel to the respective ADC. When using a multiplexer, one ADC 33 may be used to convert the input signal of every channel one after the other. Using the multiplexer, several input channels can be sampled sequentially with one ADC. In a possible implementation, e.g. an ECG device, two ADCs may be present operable to sample e.g. five ECG input channels sequentially per ADC for a total of ten input channels.

A digital interface of the multichannel analog to digital converter 21 is connected to a processing unit 25 of the measurement device 11 so that the samples $c_i$ of the individual input signals $s_i$ are forwarded to the processing unit 25.

The processing unit 25 may comprise a first processor 27 and a first memory device 29 that constitute a computing device operable to perform various processing steps needed to perform measurements by the physiological measurement device 11. The processing unit 25 comprises multiple digital input filters 31. The number of input filters may correspond to the number N of channels and one digital input filter 31 may be assigned to one specific channel. The individual input filter 31 may be implemented as Finite Impulse Response (FIR) filters having filter coefficients represented by column vectors $x_i$ with i=1, . . . , N. A length K of the individual vectors $x_i$ corresponds to the number of filter coefficients of each digital filter 31. The digital filters 31 are also referred to as Input Channel Specific digital Filters (ICSFs) because they are applied to the samples $c_i$ of the input signals $s_i$ before differential output signals are derived from these samples.

The present disclosure is not limited to a specific filter topology. Instead of FIR filters other filters like Infinite Impulse Response (IIR) filters may be applied. The filters 31 may be implemented in software, i.e. a computer program stored in the memory device 29 may be programmed so that the first processor 27 executes a filter algorithm based on the filter coefficients $x_i$. The filter coefficients $x_i$ may be stored in a programmable and non-volatile section of the first memory device 29. The processing unit 25 may be accessible by the processing unit 27 (which may be implemented separately from the processing unit 25 or as a common processing unit) so that the processing unit 27 can read the samples $x_i$ and program and adjust the filter coefficients $x_i$.

The processing unit 25 is operable to calculate one or more output signals y (j=1, . . . M) from the samples $c_i$ of the individual input signals filtered by the individual digital input filters 31. The output signals $y_j$, also referred to as vector signals or just to as "vectors", may be calculated by forming a linear combination of filtered samples $\tilde{c}_i$ of multiple channels, thereby performing a differential measurement with respect to at least two input signals $s_i$. This linear combination may be specified by a definition vector $v_j$ of a specific output signal $y_j$, where $1^T*v_j=0$ and 1 stands for a column vector of ones, i.e. $1^T=[1, \ldots, 1]$ and "*" denotes the scalar product. The output signal is $y_j=y_j=c_l*v_j$. The linear combination described by the definition vector specifies a differential measurement. The differential measurement may be based on two or more channels. In some applications like ECG or EEG, the vector signals are often also referred to as "leads".

In physiology, voltage measurements are almost always differential. Other physical quantities like pressure or temperature are usually measured as absolute values (e.g. a temperature of 37° C. or an intra-arterial pressure of 100 mmHg), but in some cases, differential measurements can be of interest (cardiac output can be measured by thermodilution, which requires measuring the temperature difference at two points in a blood vessel). The here described technology can thus be applied to differential measurements that are not voltage measurements, too.

For the sake of simplicity, FIG. 4 shows only one digital filter 31 per input channel. However, it is possible to provide multiple digital filters 31 for one input channel i, each of them processing the samples $c_i$. The different digital filters 31 may be associated with different output signals. Accordingly, a specific variant of the filtered signal $\tilde{c}_l^j$ may be used for calculating a certain output signal $y_j$.

Figure 5:
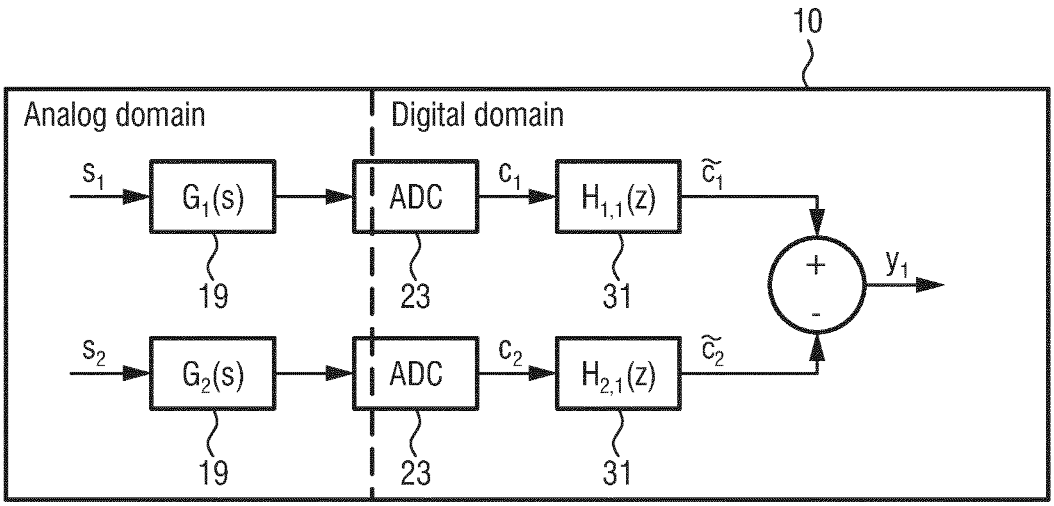
FIG. 5 shows a schematic diagram of an embodiment of recording unit according to the present invention.

FIG. 5 shows an exemplary embodiment of the recording unit 10. In this example an output signal $y_1$ is generated by subtracting a filtered input signal $s_2$ from another filtered input signal $s_i$ (definition vector [1, −1]). Accordingly, the output signal $y_1$ corresponds to a signal obtained by differential measurement based on the two input signals $s_1$ and $s_2$. When performing physiological measurements, the input signals $s_1$, $s_2$ are subject to common mode interference. In an ideal situation, subtracting the two signals $s_1$, $s_2$ from each other would eliminate the common mode part entirely. However, in practical implementation of the measurement device 11, the signal $y_1$ includes a common mode part to some extent due to differences of electrical characteristics e.g. of components 19, 21, 23 of a signal path related to the individual channels.

In electrophysiology voltages are measured that occur between points on the surface of a patient due to activity of muscle cells or nerve cells. The signals of interest are usually in the microvolt (EEG) to millivolt (ECG) range, while the common-mode component of the signal can be tens or hundreds of millivolts. In a medical context, there are many possible sources of interference (including common mode interference) ranging from other pieces of medical equipment, electronic communication or networking devices and power line noise. In order for the output signal $y_j$ to be useful for diagnosis and therapy, electrophysiological measurement devices 11 are required to have a high common mode rejection ratio (CMRR). Although there are standardized test procedures for determining the CMRR in the range of power line frequency of 50 Hz or 60 Hz, common-mode interference should also be mitigated at other frequencies. The frequencies where common-mode interference should be mitigated may include frequencies outside the ECG/EEG bands, especially if the recording device performs some kind of out-of-band processing (for example for electrode impedance measurement or ECG pacemaker pulse detection).

As explained above, the recording unit 10 records electric potentials from several electrodes. The electrodes are in contact with the patient's tissue, usually by the means of an implanted electrode array (external electrodes, e.g. adhesive or needles, may also be used). Each electrode is connected to analog input circuitry within the device. The analog input circuitry usually contains a low-pass filter, but may also contain other filter characteristics like high-pass or band-stop filters. Due to the use of real components, the analog input circuitry is subject to component tolerances, which lead to impedance mismatch. This is one source of common-mode to differential-mode conversion. Another source of common-mode to differential-mode conversion is the impedance of the tissue-electrode interface. This impedance may also vary slowly over time if the electrode-tissue interface degrades.

After passing through the analog input circuitry, each electrode signal (also called measurement signal or input signal) is converted to digital form using an analog-to-digital converter. The conversion occurs in single-ended mode, which means that the electrode signal is reference against an internal, stabilized electric potential. After analog-to-digital conversion, each electrode signal passes through a digital filter with adjustable coefficients. After this filter, vectors ("differences"/"leads") are formed from the individual electrode signals, and the vectors contain the information that is used to evaluate the progress of the therapy.

The stimulation unit 20 emits stimulation signals $w_k$ (k=1, . . . , K) via the output channels 22 to the stimulation electrodes, which cause activation of electrically excitable tissue (usually nerve tissue). The stimulation waveforms usually have a relatively large amplitude in order to reliably cause tissue excitation. The stimulation signal also causes a large common-mode signal at the inputs of the recording unit 10, specifically any input electrodes that are not used as outputs for the stimulation pulse.

To mitigate common-mode interference, the digital filters 31 may be designed such that a common-mode part of the respective output signals $y_j$ is minimized. To this end the processing unit 27 shown in FIG. 4 can be applied to determine/adjust the filter coefficients $x_i$ so that the common-mode component of the individual output signals $y_j$ are minimized.

As the physiological measurement device 11, in particular the stimulation unit 20, controls the timing and waveform of the stimulation, single-ended electrode data when stimulation occurs can be recorded as measurement signals. Updated filter coefficients $x'_i$ can then be calculated by the processing unit using the single-ended data samples, prior knowledge of expected signal and noise waveforms, and the current filter coefficients $x_i$. This can be done in a sample-by-sample basis using algorithms like least-mean-squares (LMS) or recursive-least-squares (RLS), or block-wise using optimization algorithms.

The prior knowledge may be known properties of physiological waveforms, for example frequency domain properties or statistical properties. A frequency domain property would be knowledge that the energy of the signal of interest is mostly contained within a known frequency range. Statistical properties vary between different measurement types. ECG signals, for example, are sparse, which means that many samples of an ECG wave are equal or close to zero. The derivatives of ECG signals with respect to time are also sparse, i.e., the slope and the curvature of ECG signals are frequently close to zero. Sparsity of the derivatives implies that the signal has a structure in time. In statistical terms, sparsity implies that the probability density function is leptokurtic/supergaussian. The probability density function of ECG signals is also usually asymmetric, which results in a skewness value that is not close to zero. Additionally, some time domain properties of ECG signals are known, for example that the absolute value of the slope is usually below 350 mV/s.

Other measurements may have different properties. Electromyographic signals, for example, are also usually sparse (recognizable segments of activity and inactivity) and hence leptokurtic. EEG signals are usually more random, i.e. they are dense instead of sparse. Measurements that can pick up single action potentials are sparse, as excitable cells have refractory periods with no activity between each action potential.

Such properties can be integrated into the cost function or constraints to find filter coefficients that result in output vector signals that coincide with the known properties. Similarly, known properties of the interfering signal (i.e. the stimulation signal) can be used to look for filter coefficients that minimize the similarity of the output vector signal with the interference. Line noise interference, for example, is usually dense (values far from zero for a large percentage of the time) and platykurtic/subgaussian.

In the embodiment shown in FIG. 4, a processing unit 27 and a memory device 29 are provided. The processing unit 27 may include Input/Output (IO) circuitry configured for accessing the memory device 29, in particular the non-volatile section thereof, so that it can read the current filter coefficients $x_i$ and adapt the filter coefficients $x_i$. The IO circuitry is configured for performing IO operations to access data present in the measurement device 11 and/or to control the measurement device to carry out a herein described method.

The cost function that is minimized may be chosen to reflect the magnitude of the common-mode interference. In an embodiment, this could mean a simple measure like the energy contained in the vector signals. The optimization can also be subject to constraints, for example to ensure that the differential-mode gain (responsible for accurate reproduction of the signal of interest) is not reduced, or to limit the values of the calculated filter coefficients to avoid overflow. In general, the filter coefficient calculation happens while the device is in use on a patient.

In one embodiment, as shown in FIGS. 4 and 5, each channel has exactly one digital filter 31. The filter samples $\tilde{c}_l$ generated by these filters 31 are used to calculate every output signal $y_j$ corresponding to a specific vector or lead. In a different embodiment at least one channel has at least two sets of filter coefficients corresponding to different digital filters. These filters may be used to calculate one or more specific output values. For instance, a first digital filter is used to calculate a first output signal and a second digital filter is used to calculate a second output signal. Both digital filters are configured to filter the input signal of one channel. In an embodiment, each output signal $y_j$ has a dedicated set of digital filters 31. In other words, the set of filter coefficients corresponding to the individual digital filters 31 are obtained for a specific vector corresponding to the output signal $y_j$.

Figure 6:
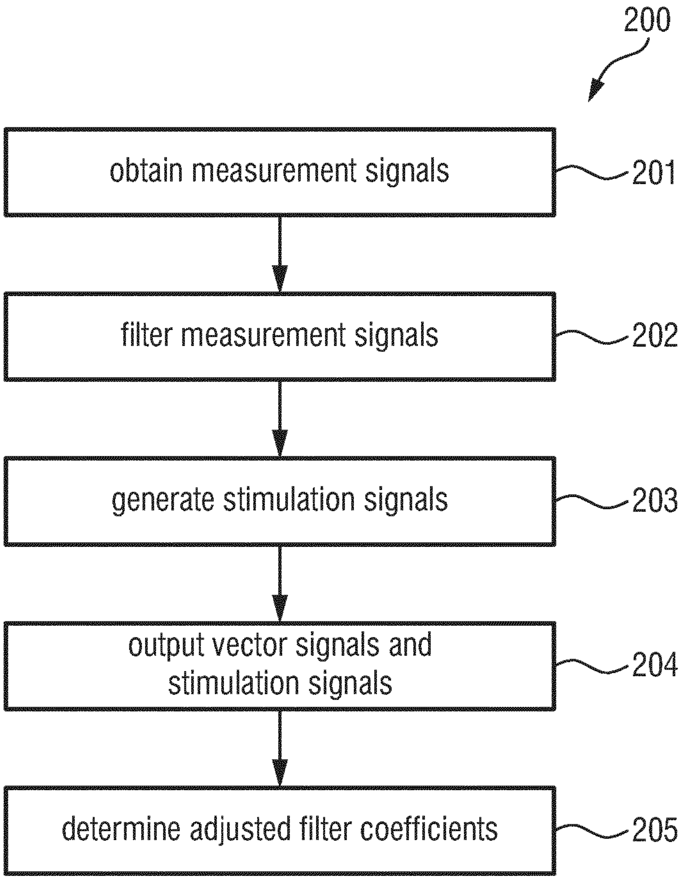
FIG. 6 shows a schematic diagram of an embodiment of a method according to the present invention.

FIG. 6 shows a flow chart of an embodiment of a physiological measurement method 200 according to the present invention, which is e.g. carried out by the physiological measurement device 11. In a first step 201 multiple measurement signals acquired from a subject are obtained (received or retrieved). In a second step 202 the multiple measurement signals are filtered by use of a digital filter and multiple vector signals are calculated from the multiple filtered measurement signals. In a third step 203 one or more stimulation signals for electrically stimulating tissue of the subject are generated. In a fourth step 204 the multiple vector signals and the one or more stimulation signals are outputted. In a fifth step 205 adjusted filter coefficients of the digital filter are determined during or after the generation and output of the one or more stimulation signals based on the current filter coefficients, the one or more stimulation signals and the multiple measurement signal acquired while the one or more stimulation signals are outputted for stimulation. Afterwards the method proceeds with step 201, wherein in step 202 the adjusted filter coefficients are used for filtering.

It shall be noted that the adjustment of the filter coefficients is only carried out if stimulation signals are generated and outputted. Further, the adjustment of the filter coefficients may not always be carried out when stimulation signals are generated and outputted, but may be carried out a regular or irregular intervals or randomly or only in response to a particular trigger or instruction.

Figure 7:
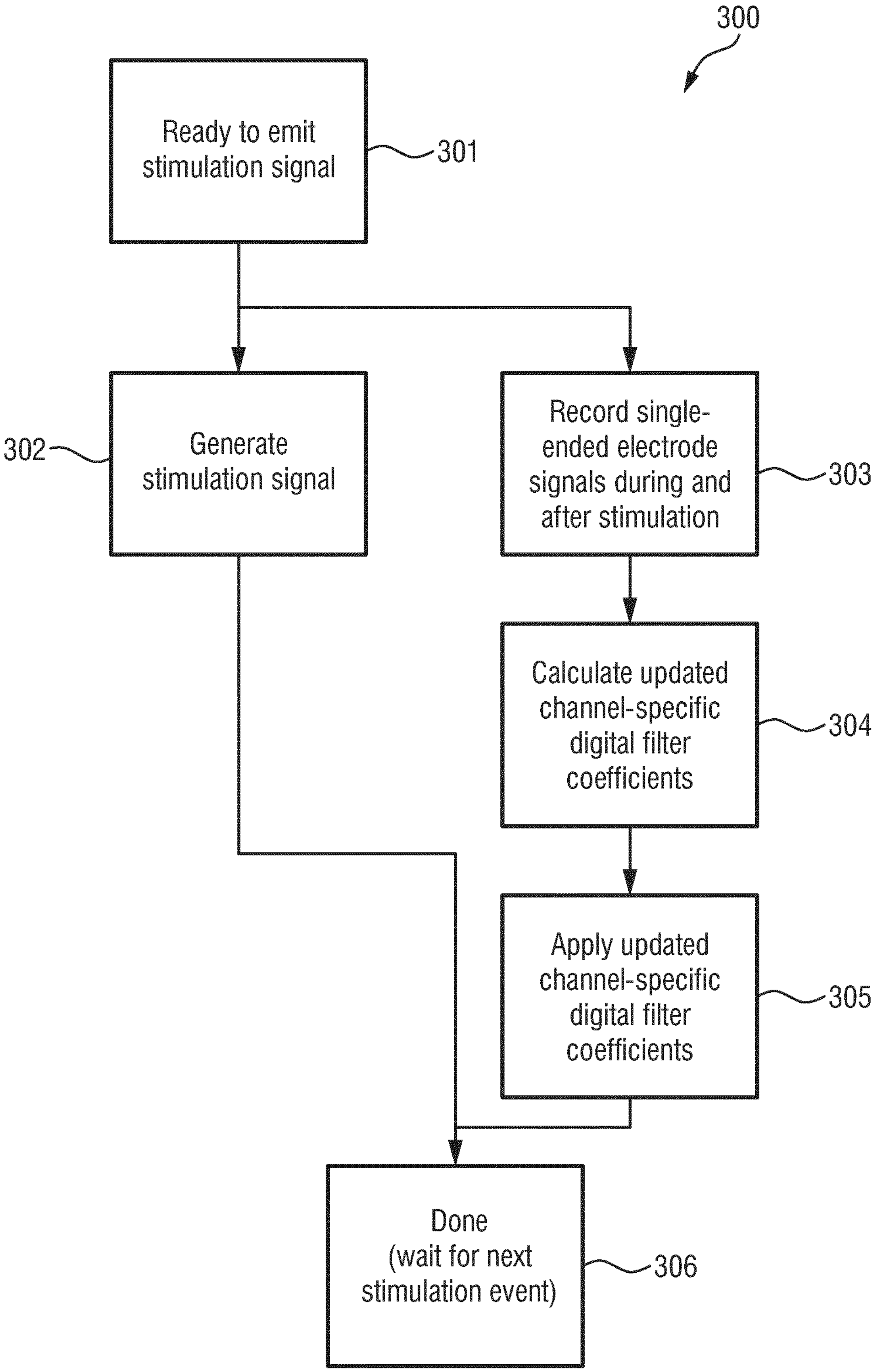
FIG. 7 shows a schematic diagram of another embodiment of a method according to the present invention.

FIG. 7 shows a flow chart of another embodiment of a physiological measurement method 300 according to the present invention. In a first step 301 the device is checked or prepared to be ready to emit a stimulation signal. If it is ready, in a second step 302 a stimulation signal is generated. In parallel, in a third step 303 single-ended electrode signals are recorded during (and optionally after) stimulation, in a fourth step 304 updated channel-specific digital filter coefficients are calculated, and in a fifth step 305 the updated channel-specific digital filter coefficients are applied.

Finally, in a sixth step 306 the method is ended and waits for the next stimulation event. In this waiting time, electrode signals from the measurement electrodes can be recorded and processed with the updated filter coefficients.

Figure 8:
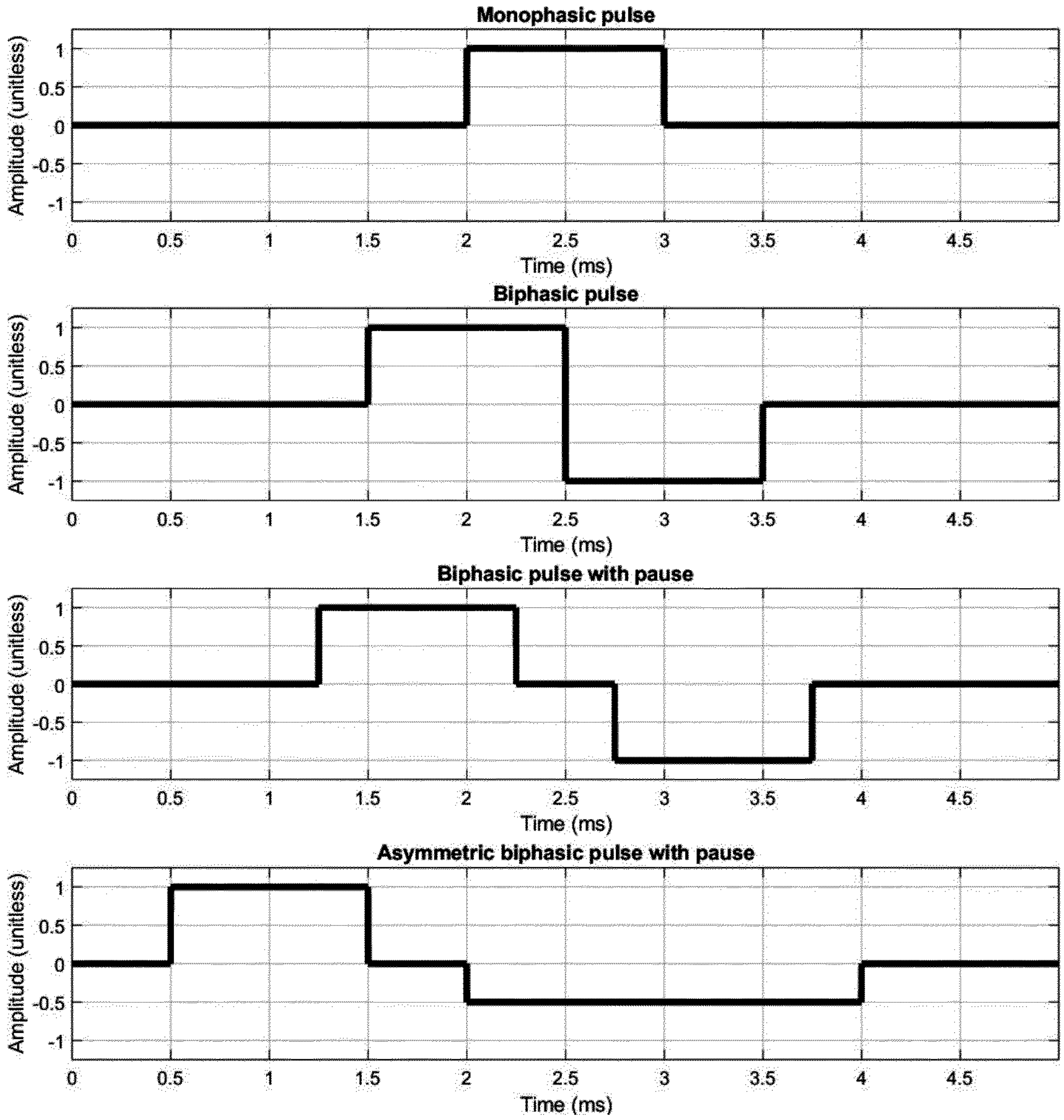
FIG. 8 shows examples of stimulation waveforms.

FIG. 8 shows various examples of stimulation signals. Stimulation signals may generally be rectangular biphasic or monophasic pulses that are frequently used for electric stimulation. Other waveforms, such as decaying exponentials, trapezoids, or sine waves, may be used as well. The present invention does not imply or presuppose any particular stimulation waveform. The stimulator design can use almost any waveform that achieves the desired stimulation, without making any concessions or compromises for the calibration. Usually, this will mean rectangular pulses followed by a longer, smaller section with inverted polarity (in order to make the average current over time zero). It can also mean a rectangular pulse followed by a similar rectangular pulse with inverted polarity ("biphasic stimulation"). The two pulses can also be separated by a brief isoelectric section. More complex stimulation patterns can be formed by a sequence of such pulses.

Generally, one stimulation signal provided to all input channels. Only a single stimulation signal is applied to the patient through the stimulation output electrodes. The appearance of this signal at each of the input electrodes is slightly different due to the differences in the input transfer functions, but each input channel signal is still a rendering of the same stimulation signal. So there are at least two single-ended input channel signals.

A stimulation signal is usually much larger in amplitude than the bioelectric signals that the recording unit picks up. Depending on the application, the stimulation signal is either delivered via electrodes that are only used for this purpose, or via electrodes that are also used as recorder inputs outside the periods where stimulation occurs.

The present invention makes use of the fact that the stimulation signal often appears as a large common-mode component at the input electrodes. However, due to the analog parts of the input channels (G1, G2 in FIG. 5) being slightly different, the original common-mode component is no longer equal at the ADCs—this is also referred to as common-mode to differential-mode conversion. When a difference/vector is formed using the raw ADC signals, a portion of the common-mode component will appear in the difference signal.

The device according to the present invention has access to the raw samples of the ADCs, as well as the calculated difference signal y, which is the difference of the ADC signals after being processed by the equalization filters. For samples affected by the stimulation signal, the device can seek filter coefficients that minimize some measure (e.g. 12-norm, supremum norm) of the magnitude of y, under a set of constraints. The result are updated filter coefficients.

According to the present invention adjusted filter coefficients of the digital filter are determined during or after the generation and output of the one or more stimulation signals based on the current filter coefficients, the one or more stimulation signals and the multiple measurement signal acquired while the one or more stimulation signals are outputted for stimulation. In an embodiment the information is used to formulate a cost function and constraints for an optimization problem. The optimization problem can then be solved with respect to the updated coefficients. For example, the deviation of the updated coefficients from the current coefficients can be penalized in the cost function, or limited by constraints. This prevents the optimizer from creating large jumps in the coefficient values.

In another example, the cost function penalizes some measure of the amplitude of the measurement signal, for example the 12/Euclidean norm. As the measurement signal during the stimulation pulse contains significant amounts of common-mode interference, minimizing its amplitude with respect to the filter coefficients will result in updated coefficients that provide better common mode rejection also when no stimulation signal is applied.

In another example, the deviation of the updated coefficients from some initial or nominal values can be penalized or limited. This excludes solutions that are too far from those that are known to be acceptable.

In another example, the maximum of the covariance of the stimulation signal and the measurement signals can be penalized. This would be an advanced implementation compared to just penalizing the amplitude of the measurement signals during stimulation.

In another example, the start and duration of the stimulation events is known. This is used to trigger the recording of measurement data that is likely to contain a large common-mode component from the stimulation pulse.

In the following, an exemplary implementation of the optimization problem, the cost functions and constraints will be described. The following notation will be used:

a, b, c: scalars b, x, y: column vectors

A, B, X: matrices 0, 1: vectors of all zeros and all ones, respectively $b^T$, $x^T$: Transposed vectors $\| \ldots \|_2$: 12-norm, Euclidean norm $\| \ldots \|_1$: 11-norm $\| \ldots \|_\infty$: Supremum norm, Chebyshev norm, uniform norm A general FIR filter may be defined as follows $$b = [b_0 b_1 \ \ldots \ b_m]^T \text{(filter coefficient vector, length } m+1)$$

$$x(n) = [x(n)x(n-1) \ \ldots \ x(n-m)]^T \text{(input data vector)}$$

$$y(n) = b_0 x(n) + b_1 x(n-1) + \ldots \ + b_m x(n-m) = b^T x \text{(filter output)}$$

The difference of two filtered signals is as follows:

$$y_{diff}(n) = y_1(n) - y_2(n) = b_1^T x_1 - b_2^T x_2 = \left[x_1^T x_2^T\right] \cdot \begin{bmatrix} b_1 \\ b_2 \end{bmatrix}$$

The last form is useful when the vectors b are unknowns or optimization variables.

The output vector $y_{diff}$ containing samples at several points in time can be expressed as $$y_{diff} = \begin{bmatrix} x_1^T(n) & x_2^T(n) \\ x_1^T(n+1) & x_2^T(n+1) \\ x_1^T(n+2) & x_2^T(n+2) \\ \ldots & \ldots \end{bmatrix} \cdot \begin{bmatrix} b_1 \\ b_2 \end{bmatrix} = [\, X_1 \quad X_2 \,] \cdot \begin{bmatrix} b_1 \\ b_2 \end{bmatrix} = X \cdot \begin{bmatrix} b_1 \\ b_2 \end{bmatrix} = X \cdot b$$

$y_{diff}$ corresponds to $y_1$. The anti-diagonals matrices $X_1$ and $X_2$ contain the same value, i.e. the matrices are Hankel matrices. By reversing the order of the coefficients in the vectors b, $X_1$ and $X_2$ can be converted into the more familiar form of Toeplitz matrices that contain the same value on each diagonal. This does not change the equations or the solution.

The optimization problem for updating filter coefficients may be implemented as follows: Record $x_1$ and $x_2$ during stimulation events. Form matrix X from this data by arranging the contents of $x_1$ and $x_2$ in matrix. As each x can be thought as being the sum of a common-mode component (e.g. $x_{1,cmi}$) and a differential-mode component ($x_{1,dm}$), the matrix X can likewise be expressed as $X=X_{dm}+X_{cm}$, with $X_{cm}$ being significantly larger than $X_{dm}$ in some matrix norm sense during stimulation events.

The general optimization goal may be: minimize $\|X \cdot b\|$ with respect to b, since during stimulation events, the differential-mode signal is small, the common-mode signal is large, and the change (gradient) of the norm with regard to b is mainly determined by the common-mode signal component. Use constraints and regularization to avoid solutions that are not useful (e.g. b=0) and to impart required properties on the filter coefficients, like minimal attenuation of the signal of interest.

An example of a cost function can be formulated as:

$$f_c(b) = \|X \cdot b\|_2^2 + \gamma \cdot \|b - b_{initial}\|_2^2$$

This uses the square of Euclidean norms as this results in an optimization problem that is easier to solve numerically and may even have a closed-form solution. Besides penalizing the magnitude of the output vector $y_{diff}$, the cost function also penalizes the deviation of the vector of filter coefficients from some initial condition. This regularization serves both to improve numeric behavior if the matrix X is ill-conditioned or underdetermined, and to limit the deviation from the initial coefficient values $b_{initial}$. $b_{initial}$ may be a set of nominal values determined at design time of the device, or correspond to the current set of filter coefficients, thus penalizing large steps away from the current coefficients. The factor $\gamma$ is used to adjust the trade-off between minimizing common-mode to differential conversion and the solution staying close to $b_{initial}$.

Constraints can be used to impart required properties on the solution. For example, equality constraints of the form $$1^T b_k - c = 0$$

can be used to constrain the gain of the equalization filter $b_k$ to c at f=0 Hz. As the signal of interest is usually located near 0 Hz (relative to the total frequency range), one such constraint for each equalization filter ensures that the equalization filter does not significantly attenuate the signal of interest.

If the required gain at f=0 Hz is not known exactly, pairs of inequality constraints of the form $$1^T b_k - c \le 0$$

$$-1^T b_k + d \le 0$$

can be used to constrain the gain at f=0 Hz to lie in the closed interval [d; c]. This gives the optimization algorithm some freedom as far as the gain at 0 Hz is concerned.

The gain at frequencies f other than 0 Hz can be constrained with inequality constraints of the form $$\|W_f \cdot b_k\| - c \le 0$$

with $$W = \begin{bmatrix} \sin(0\omega) & \sin(1\omega) & \sin(2\omega) & \dots \\ \cos(0\omega) & \cos(1\omega) & \cos(2\omega) & \dots \end{bmatrix}, \omega = 2\pi \frac{f}{f_{sampling}}$$

This only allows constraining the gain to be less-or-equal to some value while preserving the convexity of the optimization problem. Equal- or greater-or-equal constraints will result in a nonconvex optimization problem.

Bounds constraints on the filter coefficients of the form $b_i$<=c and $b_i$>=d (usually with d=−c and c positive) can be used to constrain the value of the coefficients to the range of the data type used for storing them, or to a lower absolute value to avoid numerical overflow during the calculation of the filter output value. Many commercially and freely available optimization packages accept bounds constraints as input, which may result in more effective computation compared to listing bounds constraints among the general constraint inputs. More elaborate bound constraint setups can be used to constrain the deviation of the optimization result from some nominal or initial filter coefficient vector.

The optimization problem should be formulated as a convex optimization problem if possible, which means the cost function to be minimized should be convex, the inequality constraints should be convex, and the equality constraints should be affine ("linear" is not entirely correct, but often used synonymously to "affine" colloquially).

In summary, the present invention improve the input channel symmetry of electrophysiological recorders which are part of, combined with or used together with electrophysiological stimulation devices. The stimulating action of such devices causes a substantial, undesired common-mode signal component. As the timing and the waveform of the stimulation is known, the individual input channel digital filter coefficients can be calculated, which compensate the existing input channel asymmetry. This makes the device, in particular the recorder, less sensitive to common-mode interference from any source—not only the interference cause by the stimulator function, but also to interference from unknown external sources. Less sensitivity to interference improves the therapeutic benefit of therapeutic devices like closed-loop neuromodulators and the reliability of non-therapeutic devices like brain-machine interfaces.

The present invention is particularly applicable in electrophysiological stimulation devices which also contain electrophysiological recording functionality, and where the effect of the stimulation causes a substantial common-mode signal at the input of the recorder component.

One group of devices is closed-loop neuromodulation devices. They provide therapeutic stimulation only when and to the degree that it is necessary and need to monitor neurological signals to determine the necessity, degree and success of the therapy. Improved artefact and interference rejection improves monitoring of therapy effects and disease progress and ultimately increases the chance of therapeutic benefits. In this context, the measurement signals acquired from the subject may be used to modify and/or monitor the effect of the stimulation. For instance, stimulation parameters amplitude, timing and/or shape of the stimulation signal(s) may be adapted or controlled based on the information gained from the measurement signals that may show the effect of the stimulation.

A second group of devices is bi-directional brain-machine interfaces. Improved artefact and interference rejection improves the accuracy and reliability of information gathered from the brain and transmitted to the machine.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A physiological measurement device comprising:

multiple input channels configured to obtain multiple measurement signals ($s_i$) acquired from a subject;

a recorder configured to filter the multiple measurement signals ($s_i$) by use of a digital filter and calculate multiple vector signals ($y_i$) from the multiple filtered measurement signals, wherein a vector signal represents a differential signal and is calculated by forming a linear combination of at least two filtered measurement signals;

a stimulator configured to generate one or more stimulation signals ($w_k$) for electrically stimulating tissue of the subject;

multiple output channels configured to output the multiple vector signals ($y_i$) and the one or more stimulation signals ($w_k$); and a processor configured to determine adjusted filter coefficients of the digital filter during or after the generation and output of the one or more stimulation signals ($w_k$) based on the current filter coefficients, the one or more stimulation signals ($w_k$) and the multiple measurement signals ($s_i$) acquired while the one or more stimulation signals ($w_k$) are outputted for stimulation, wherein the digital filter is configured to filter the multiple measurement signals, after the adjusted filter coefficients have been determined, by use of the adjusted filter coefficients.

2. The physiological measurement device as claimed in claim 1, wherein the processor is configured to compute the adjusted filter coefficients on a sample-by-sample basis.

3. The physiological measurement device as claimed in claim 1, wherein the processor is configured to compute the adjusted filter coefficients by minimizing a cost function to reflect the magnitude of common-mode interference.

4. The physiological measurement device as claimed in claim 1, wherein the recorder comprises an analog filter for analog filtering of the multiple measurement signals ($s_i$), an analog-to-digital converter for converting the filtered measurement signals into digital signals and a digital filter for digital filtering of the digital signal to generate the multiple vector signals ($y_i$).

5. The physiological measurement device as claimed in claim 1, wherein the processor is configured to determine adjusted filter coefficients after each stimulation event or after a predetermined or arbitrary number of stimulation events.

6. The physiological measurement device as claimed in claim 1, further comprising a memory device configured to store multiple different sets of filter coefficients ($x_i$) related to one input channel; and wherein the processor is configured to select one of the different sets of filter coefficients ($x_i$) for determining the adjusted filter coefficients.

7. The physiological measurement device as claimed in claim 1, wherein the processor is configured to calculate multiple vector signals ($y_i$), one of said multiple vector signals being calculated from multiple filtered measurement signals based on a definition vector ($v_i$), wherein the memory device is configured to store different sets of filter coefficients ($x_i$) related to one input channel, and wherein the processor is configured to select one of the different sets of filter coefficients ($x_i$) for calculating a specific vector signal ($y_i$).

8. The physiological measurement device as claimed in claim 1, wherein the processor is configured to generate samples ($c_i$) of one or more stimulation signals applied to the multiple input channels;

input at least one definition vector ($v_i$) describing a linear combination of samples ($c_i$) of at least two input channels;

optimize a metric calculated from at least one vector signal ($y_i$), the vector signal being based on the samples ($c_i$) of the one or more stimulation signals and the definition vector ($v_i$); and obtain, based on the optimizing, at least one set of filter coefficients ($x_i$) for at least one digital filter associated with a specific input channel.

9. The physiological measurement device as claimed in claim 8, wherein the processor is configured to input multiple definition vectors ($v_i$) and to obtain at least one set of filter coefficients ($x_i$) for a specific input vector ($v_i$).

10. The physiological measurement device as claimed in claim 8, wherein the processor is configured to optimize the metric by multiple optimizing steps, wherein a set of filter coefficient obtained by one optimizing step being kept as constant for a subsequent optimizing step and/or by use of at least one linear equality constraint with respect to a filter coefficient ($x_i$) and/or by use of at least one nonlinear inequality constraint for limiting a gain of a certain digital filter at a given frequency.

11. The physiological measurement device as claimed in claim 10, wherein the processor is configured to sample the one or more stimulation signals at a sampling rate ($f_{samp}$) that is increased compared to an operating sampling rate applied to perform physiological measurements by the physiological measurement device and/or with a resolution (res) that differs from a measurement resolution of samples received to perform the physiological measurements.

12. The physiological measurement device as claimed in claim 8, wherein the processor is configured to optimize the metric by minimizing a penalty function of output samples ($y_i$), the output samples corresponding to at least one vector signal ($y_i$) calculated from the stimulation signal filtered according to the filter coefficients ($x_i$) and from the definition vector ($v_i$).

13. A physiological measurement system comprising:

multiple measurement electrodes configured to acquire multiple measurement signals ($s_i$) from a subject;

a physiological measurement device as defined in claim 1;

multiple stimulation electrodes configured to apply one or more stimulation signals ($w_k$) generated by the physiological measurement device to the subject for electrically stimulating tissue of the subject; and an output configured to output multiple vector signals ($y_i$) calculated by the physiological measurement device.

14. A physiological measurement method comprising:

obtaining multiple measurement signals acquired from a subject;

filtering the multiple measurement signals by use of a digital filter and calculate multiple vector signals from the multiple filtered measurement signals, wherein a vector signal represents a differential signal and is calculated by forming a linear combination of at least two filtered measurement signals;

generating one or more stimulation signals for electrically stimulating tissue of the subject;

outputting the multiple vector signals and the one or more stimulation signals;

determining adjusted filter coefficients of the digital filter during or after the generation and output of the one or more stimulation signals based on the current filter coefficients, the one or more stimulation signals and the multiple measurement signals acquired while the one or more stimulation signals are outputted for stimulation; and filtering the multiple measurement signals, after the adjusted filter coefficients have been determined, by use of the adjusted filter coefficients.

15. A non-transitory computer readable medium that stores therein a computer program product, which, when executed on a processor, causes the method as claimed in claim 14 to be performed.

16. The physiological measurement device as claimed in claim 2, wherein the sample-by-sample basis is a least-mean-squares algorithm, a recursive-least-squares algorithm, or block-wise using an optimization algorithm.

17. The physiological measurement device as claimed in claim 4, wherein the analog-to-digital converter is in single-ended mode.

18. The physiological measurement device as claimed in claim 12, wherein the processor is configured to optimize the metric by minimizing a penalty function of output samples ($y_i$) by minimizing multiple different penalty functions of the output samples ($y_i$) simultaneously or minimizing a scalar target function of different penalty functions.

* * * * *